United States Patent
Biel

(10) Patent No.: US 6,251,127 B1
(45) Date of Patent: Jun. 26, 2001

(54) DYE TREATMENT SOLUTION AND PHOTODYNAMIC THERAPY AND METHOD OF USING SAME

(75) Inventor: Merrill A. Biel, Mendota Heights, MN (US)

(73) Assignee: Advanced Photodynamic Technologies, Inc., Mendota Heights, MN (US)

(*) Notice: Subject to any disclaimer, the term of this patent is extended or adjusted under 35 U.S.C. 154(b) by 0 days.

(21) Appl. No.: 09/139,866

(22) Filed: Aug. 25, 1998

Related U.S. Application Data

(60) Provisional application No. 60/057,356, filed on Aug. 25, 1997.

(51) Int. Cl.[7] .................................................. A61B 18/18
(52) U.S. Cl. ................................ 607/88; 607/89; 606/2; 606/3; 606/11
(58) Field of Search ..................... 606/1, 2, 3, 9, 606/10, 11, 12, 14, 15, 16, 17, 19; 607/88, 89

(56) References Cited

U.S. PATENT DOCUMENTS 4,951,663 * 8/1990 L'Esperance, Jr. ..................... 606/10
5,611,793 * 3/1997 Wilson et al. .......................... 606/2

* cited by examiner

Primary Examiner—Linda C. M. Dvorak
Assistant Examiner—Sonya Harris Ogugua
(74) Attorney, Agent, or Firm—Larkin, Hoffman, Daly & Lindgren, Ltd.; John F. Klos

(57) ABSTRACT

The invention relates to a method of treating an infection or sterilization including applying a dye such as methylene blue, toluidene blue, polymyxin B, or combinations thereof to the area of infection or area to be sterilized and exposing the area of infection or area of sterilization with a light having a light wavelength and light dosage and a light dosage rate. The dye may have a concentration ranging from about 10 μg/ml to about 500 μg/ml. The wavelength may range from about 610 nm to about 670 nm. The light dosage may range from about 0 J/cm$^2$ to about 200 J/cm$^2$. The light dosage rate may range from about 0 mw/cm$^2$ to about 150 mw/cm$^2$. The treatable infections include staphylococcus, *Candida albicans*, *Escherichia coli*, enterococcus, streptococcus, *Pseudomanus aeruginosa*, *Hemophilus influenzae*, or *E-coli*. The invention also relates to an infection treatment kit.

19 Claims, 3 Drawing Sheets

DYE TREATMENT SOLUTION AND PHOTODYNAMIC THERAPY AND METHOD OF USING SAME

CROSS REFERENCE TO RELATED APPLICATION

This application claims the benefit of priority pursuant to 35 USC §119(e)(1) from the provisional patent application filed pursuant to 35 USC §111(b): Ser. No. 60/057,356 on Aug. 25, 1997.

BACKGROUND OF THE INVENTION

The invention relates to use of a dye treatment solution with a photodynamic therapy (PDT) treatment device. More specifically, the invention relates to photodynamic inactivation of bacteria and fungal wound infections and sterilization of tissue using methylene blue or toluidene blue and a flexible conforming patch or pad and a shaped article which provides light sources for topical PDT. The present invention advantageously uses light energy in combination with photosensitizing agents to treat or detect pathologies of living tissue, including cancer and microbiological pathogens.

U.S. Pat. No. 4,822,335, entitled, Apparatus For Treatment Of Cancer With Photodiode, purportedly discloses an apparatus for the treatment of a cancerous lesion part by irradiating a light energy from a light source to the cancerous lesion part having absorbed and accumulated in advance therein a photosensitive substance with an affinity for tumors. The light source comprises a first diode adapted to excite the photosensitive substance from the ground state to a singlet state of higher energy level and a second photodiode adapted to excite an energy level of the photosensitive substance which has transited from the singlet state to a triplet state to a still higher energy level.

U.S. Pat. No. 5,358,503, entitled, Photo-Thermal Therapeutic Device and Method, purportedly discloses an apparatus for simultaneous or selective treatment of an area of the skin and adjacent subcutaneous structure of a patient utilizing photo energy and therapeutic heat, which includes a plurality of juxtaposed diodes. Each diode has a longitudinal axis and is capable of projecting a non-coherent cone of light which overlaps the cone of light from each juxtaposed diode so that the light completely covers the treatment area. A flexible pad or appliance holds the diodes in juxtaposed position with each other.

U.S. Pat. No. 5,611,793, entitled, Laser Treatment, purportedly discloses a method of disinfecting or sterilizing tissues of the oral cavity or a wound or lesion in the oral cavity. The method includes applying a photosensitizing compound to the tissue and irradiating with laser light at a wavelength absorbed by the photosensitizing compound.

All documents cited herein, including the foregoing, are incorporated herein by reference in their entireties for all purposes.

SUMMARY OF THE INVENTION

The invention relates to use of methylene blue and toluidene blue as a photosensitizing agent in combination with a PDT treatment device for treatment of bacterial or fungus infections. The treatment device is configured to deliver light energy to an infection from a plurality of light emitting members disposed in the device. The treatment device includes light emitting members which operate at wavelengths ranging from about 450 nm to about 850 nm; provide a dosage rate ranging from about 0 to about 150 mw/cm$^2$; and provide a light dose ranging from 0 to about 300 J/cm$^2$.

The use of methylene blue or toluidene blue combined with mediated PDT advantageously acts as a broad spectrum antimicrobial, i.e., antibacterial and antifungal agent when used as a topical treatment for acute and chronic wound infections or for the sterilization of acute wounds and skin. The dye and PDT may be used, for example, before an operation. The present invention advantageously results in the destruction of gram positive and gram negative bacteria and fungus. Importantly, the present invention acts to destroy antibiotic resistant bacteria and works as a different destruction mechanism than antibiotics.

Microbiological data includes testing results of methylene blue and toluidene blue and PDT showing the efficacy of destruction of *Staphylococcus aureus* in in-vivo infected wounds; in vitro destruction of antibiotic resistant staphylococcus, streptococcus, enterococcus, *E-coli*, pseudomonas, *Hemophilus influenza* and *Candida albicans*; and wavelength spectrum of activation of methylene blue and toluidene blue in the presence of various concentrations of the above bacteria and candida.

Results show that at fixed concentrations of dye, total eradication of the bacteria or fungus requires proportionally increased total light administration (Joules) as the bacteria or fungus concentration is increased.

The present invention may be used in conjunction with or in relation to inventions disclosed in the following applications, filed on the same date concurrently herewith, Aug. 25, 1998.

U.S. patent applications: M. Biel, Inventor:

Method of Enhancing Photodynamic Therapy by Administering an Immunologic Adjuvant, Ser. No. 09/139,861.

Spatial Orientation Grid and Light Sources and Method of Using Same for Medical Diagnosis and Photodynamic Therapy, Ser. No. 09/139,862, now U.S. Pat. No. 6,048,359.

Rectangular Laser Irradiation Field Producing Apparatus for Medical Treatment, Ser. No. 09/139,480.

Methylene Blue and Toluidene Blue Mediated Fluorescence Diagnosis of Cancer, Ser. No. 09/139,481.

PCT patent application No. PCT/US98/17589 entitled, Treatment Device For Topical Photodynamic Therapy And Method Of Making Same, filed in the United States Receiving Office. M. Biel, Inventor.

All documents within these applications are herein incorporated by reference in their entireties for all purposes.

In sum, the invention relates to a method of treating an infection including identifying an in-vivo area of infection; applying a concentration including at least one of methylene blue, toluidene blue, polymyxin B, or combinations thereof to the area of infection; and exposing the area of infection with a light having a light wavelength, light dosage and a light dosage rate. The light wavelength may range from about 610 nm to about 680 nm. The light dosage may range from about 30 J/cm$^2$ to about 60 J/cm$^2$. The light dosage rate may range from about 50 mw/cm$^2$ to about 150 mw/cm$^2$. The wavelength may range from about 630 nm to about 664 nm. The concentration may range from about 10 μg/ml to about 500 μg/ml. The concentration may range from about 10 μg/ml to about 250 μg/ml; the light wavelength may range from about 630 nm to about 670 nm; the light dosage may range from about 20 J/cm$^2$ to about 60 J/cm$^2$; and the light dosage may rate range from about 50 mw/cm$^2$ to about 150 mw/cm$^2$. The concentration may range from about 50

μg/ml to about 250 μg/ml; the light dosage may range from about 30 J/cm² to about 60 J/cm²; and the light dosage rate may range from about 100 mw/cm² to about 150 mw/cm². The concentration may be about 250 μg/ml; the light dosage may be about 60 J/cm²; and the dosage rate may be about 150 mw/cm². The infection may include gram positive and gram negative bacteria and fungus including, but not limited to, at least one of staphylococcus, *Candida albicans, Escherichia coli,* enterococcus, streptococcus, *Pseudomanus aeruginosa, Hemophilus influenzae,* or *E-coli.*

The invention also relates to an infection treatment kit including a volume of a concentration including at least one of methylene blue, toluidene blue, polymyxin B, or combinations thereof. The concentration ranges from about 10 μg/ml to about 500 μg/ml. Also included is a light emitting treatment device having a thickness, one or more surfaces and one or more light dosage members disposed therein. The light dosage members are configured to emit light at an infection at wavelengths ranging from about 450 nm to about 850 nm; a dosage rate ranging from about 0 to about 150 mw/cm²; and a light dose ranging from 0 to about 300 J/cm².

The invention also relates to a method of treating an infection including providing one or more cells; disposing a concentration of dye on the one or more cells; applying a light having a wavelength ranging from about 450nm to about 850nm; a dosage rate ranging from about 0 to about 150 mw/cm²; and a light dose ranging from 0 to about 300 J/cm² to the one or more cells wherein the combination of light and dye is adapted to cause intracellular enzyme deactivation of the one or more cells. The light dose may be adapted to increase permeability of the one or more cells and cause diffusion of the dye into the one or more cells. The one or more cells may be a bacteria or a fungus. The one or more cells may be gram positive or gram negative. The dye may be methylene blue, toluidene blue, or a combination thereof. The dye may be monomeric or dimeric. The dye may be adapted to attach at hydrophobic or hydrophilic sites at the one or more cells. The one or more cells may include a pathogenic organism from a gram positive or gram negative species including, but not limited to, *Candida albicans, Escherichia coli,* enterococcus, streptococcus, *Pseudomanus aeruginosa, Hemophilus influenzae,* and *E-coli.* As the concentration of dye disposed on the one or more cells is increased a proportional total concentration of light may be applied to the one or more cells. The concentration of dye may be fixed and as the concentration of the bacteria or fungus is increased, a proportionally increased total light dose administration may be provided for eradication of the bacteria or fungus. The infection may be in-vivo or in-vitro.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTIONS OF THE DRAWINGS

DETAILED DESCRIPTION OF THE INVENTION

In accordance with the invention, a photosensitizing agent such as methylene blue or toluidene blue is applied to a treatment area and a treatment device 20 such as a patch, pad or shaped article such as a mouthpiece is used to treat the surface or tissue with PDT.

PDT eradication of candida albicans in-vitro has been achieved using medical dyes such as methylene blue and toluidene blue. Concentrations of azole resistant *Candida albicans* at 10 log8 CFU in solution were eradicated after a single treatment at total light doses of 60 Joules/cm² using methylene blue. Experiments were performed where the dye concentration was varied from 0 μg/ml to 200 μg/ml. In all cases, the azole resistant *Candida albicans* showed very little growth after treatment. The addition of clotimazole to methylene blue did not result in any change in candida survival after light activation (data not shown).

PDT eradication of *E-coli* and *Streptococcus pneumoniae* in-vitro was achieved using methylene blue and 664 nm light. Concentrations of *E-coli* at 8.425 log CFU in solution were eradicated after a single treatment at total light doses of 40 Joules/cm². Concentrations of *Streptococcus pneumoniae* at 8.40 log CFU in solution were eradicated after a single treatment at total light doses as low as 5 Joules/cm² at a methylene blue concentration of 50 μg/ml. These in-vitro results demonstrate the effectiveness of methylene blue PDT to eradicate other gram positive and gram negative wound pathogens.

Dyes such as methylene blue and toluidine blue may also be used in combination with polymyxin and activated by light energy at about 630–660 nm wavelengths to provide broad spectrum antibiotic activity destroying both gram positive and gram-negative bacteria and fungus.

Photosensitizing dyes can be used to destroy antibiotic resistant bacteria. Methylene blue and toluidine blue in combination with polymixin when activated by 660 nm light acts as a broad spectrum antibiotic destroying both antibiotic resistant gram positive and gram negative bacteria including staphylococcus, streptococcus, *Hemophilus influenza,* enterococcus, *E coli* and pseudonomas. Preferably, the light doses are 50–150 mw/cm² and 10–60 Joules/cm² at 664 nm light. Toluidene blue is activated at the same light doses but at 630 nm light. The doses are as follows: methylene blue at 50 micrograms/ml; toluidene blue at 50 micrograms/ml; and polymyxin B at 2 micrograms/ml. The three materials may be mixed together to provide a broad spectrum antibiotic response.

Figure 1:
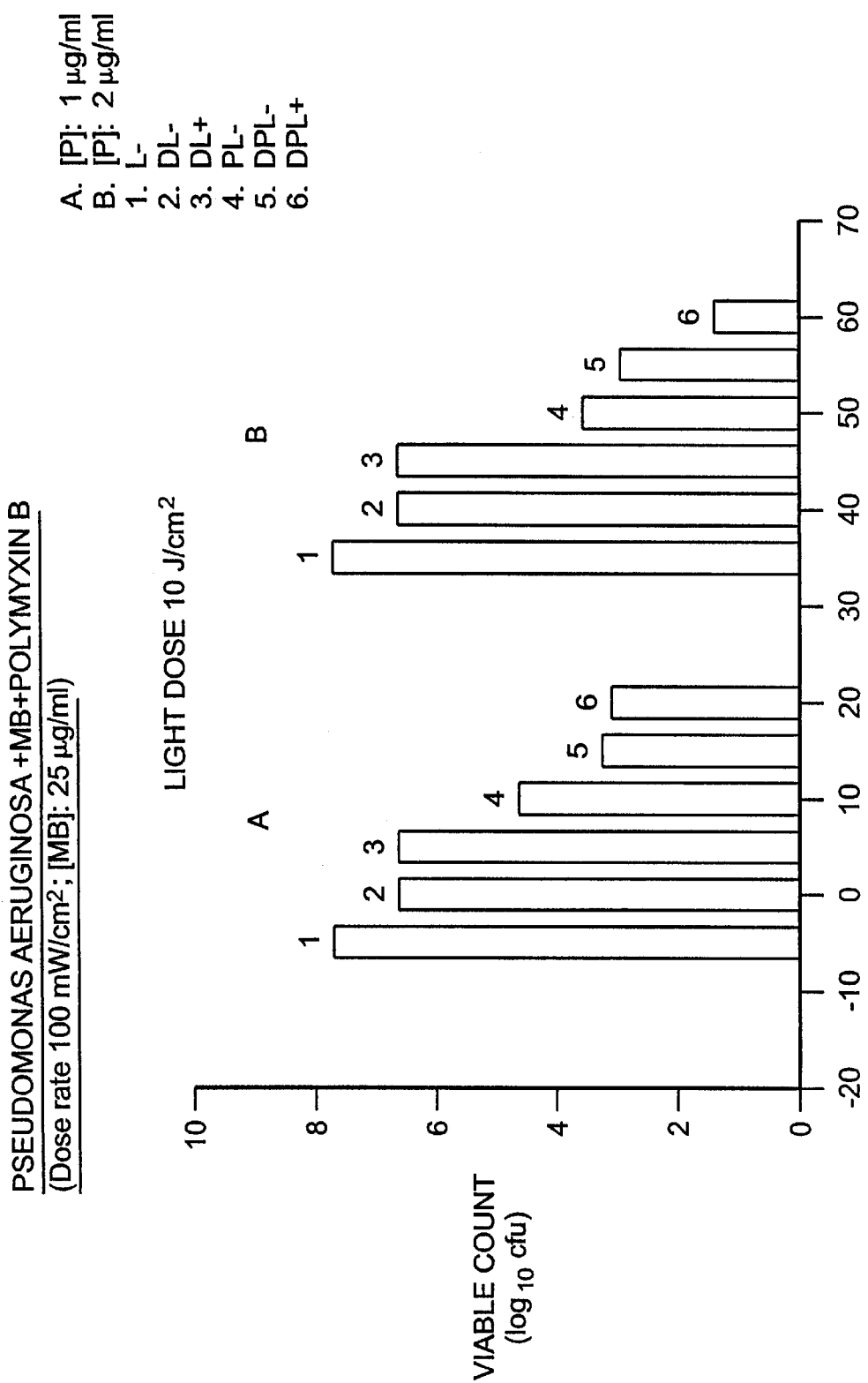
FIG. 1 is a graph showing a light dose rate of 100 mw/cm², a light dose of 10 J/cm², and a methylene blue concentration of 25 μg/ml and the variation in viable count of *Pseudomonas aeruginosa* as a function of the concentration of polymyxin B and light.
Figure 2:
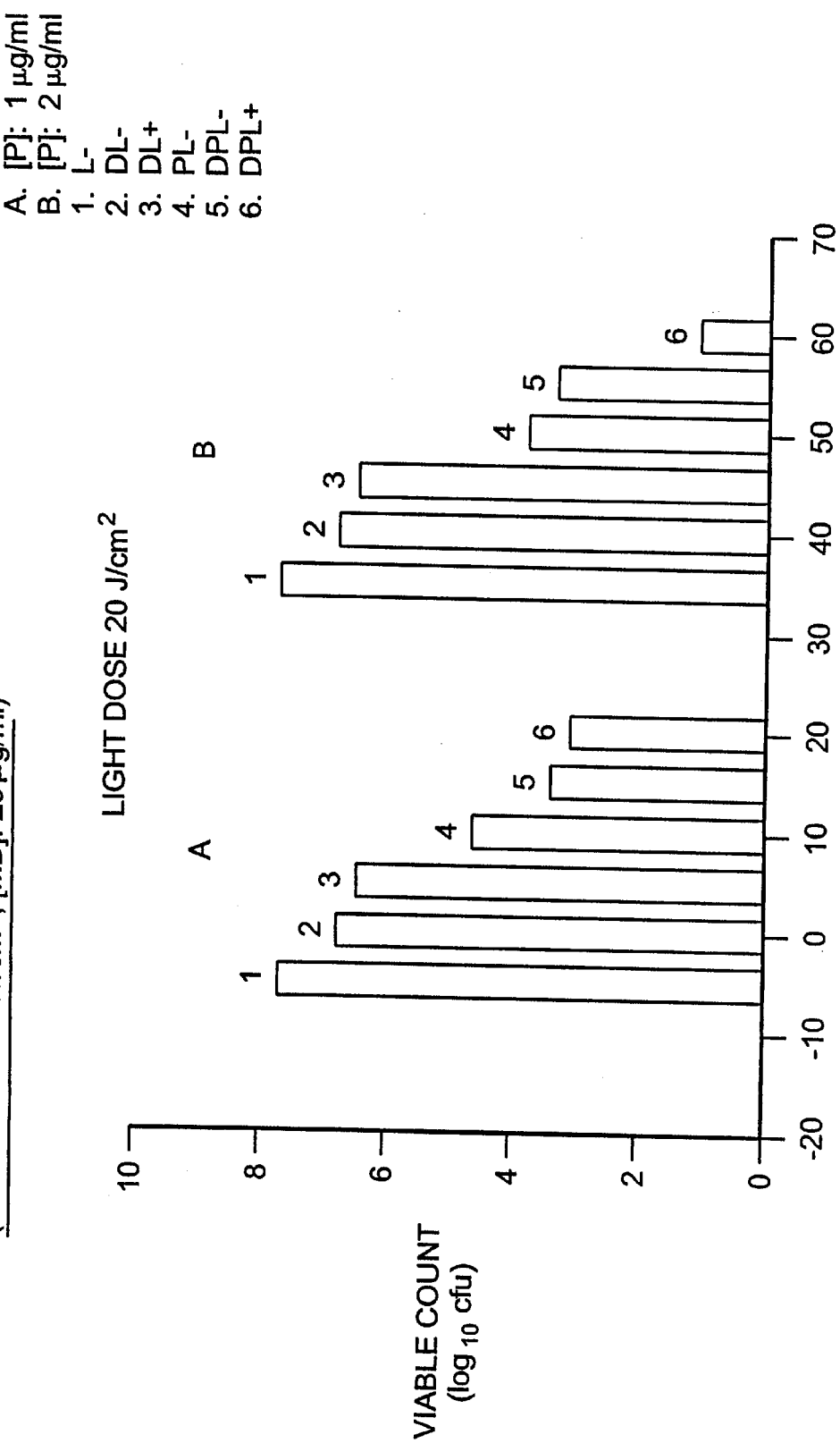
FIG. 2 is a graph showing a light dose rate of 100 mw/cm², a light dose of 20 J/cm², and a methylene blue concentration of 25 μg/ml and the variation in viable count of *Pseudomonas aeruginosa* as a function of the concentration of polymyxin B and light.
Figure 3:
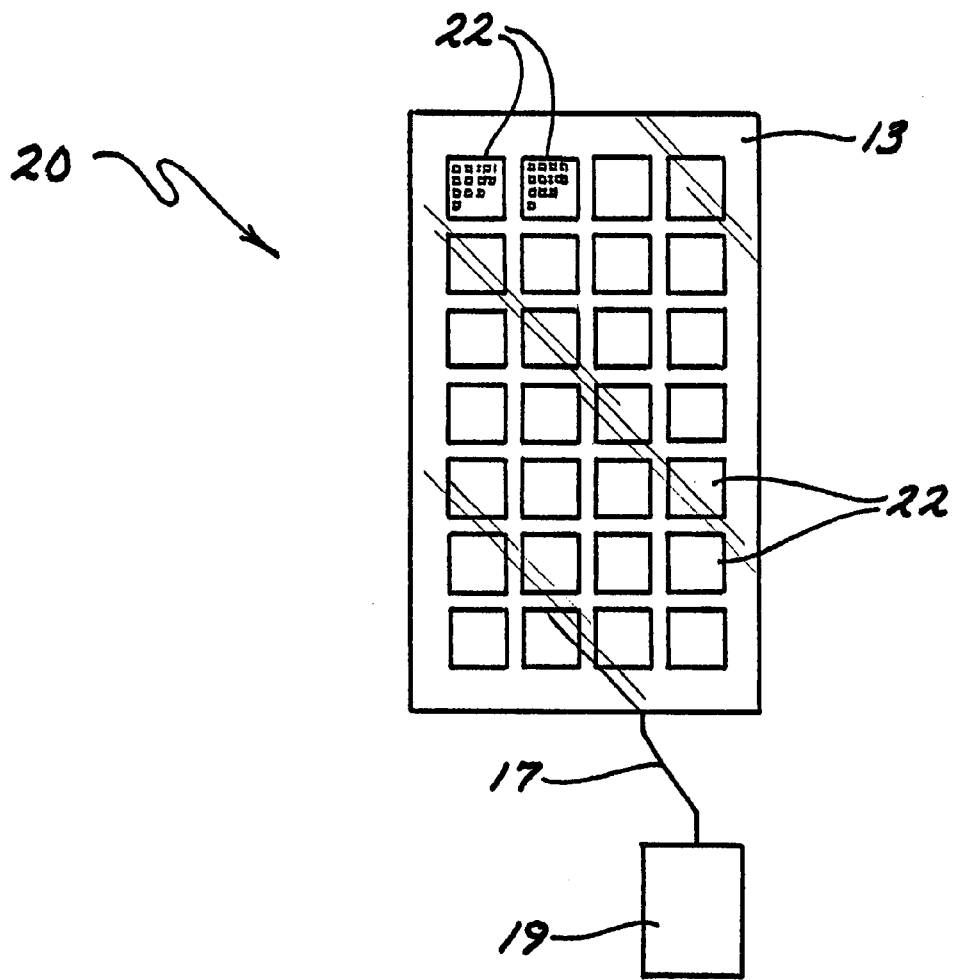
FIG. 3 illustrates a treatment device having light emitting members.

FIG. 3 illustrates a plurality of VCSELs arrayed in a treatment device 20 which is coupled to an independent power supply 14. Other light sources may also be used in the treatment device 20. A plurality of VCSELs or light emitting diodes (LEDs) are disposed in an array tile 22 or in a pattern and adhered to or mounted within a substrate 13 to form a treatment device 20. The treatment device 20 is operatively coupled to an adjustable, self-contained power source 19 such as battery using a conventional wire 17 or cable. The VCSELs 22 or LEDs in may be wired in series, parallel, or combinations of series and parallel using suitable patterns among adjacent rows or via a peripheral scheme.

The array of VCSELs may be any size, shape, or wavelength suitable for a variety of treatment applications. The number of VCSELs per treatment device may be selectively determined and varies depending upon factors including the required light output (in mw/cm$^2$). The VCSELs are separated or spaced-apart from the tissue surface by a predetermined distance dependent upon factors including the incident light energy necessary for treatment, beam divergence, and the thickness or opacity of any light-diffusing layer. The separation may be approximately 1–2 mm. The array may be flexible or rigid and configured to conform to a variety of body shapes or parts such as the tongue, palate, or cheek, as well as normally exposed skin areas having complex or irregular curvatures or tight curves, such as a patient's arm or leg, finger or toe, heel, wrist, elbow.

An embodiment of the treatment device for PDT includes a 2×8 VCSEL array light treatment device at a wavelength of 664 nm light. An embodiment of the treatment device includes a 2×8 array of 664 nm VCSELs. The maximum output light from the array is 1.4 mW (~175 µW per VCSEL) at which point the voltage is ~4V and the current per VCSEL is ~6.5 mA. A 10 degree full width at half max diffraction angle was assumed for the VCSELs. This simulation shows a good uniformity over a 4 mm$^2$ area at a distance of 10 mm. Alternatively, a diffuser may be used to improve uniformity and reduce the thickness of the device. The treatment device may be used at an appropriate wavelength to activate the dyes.

An example of the results using the present invention include the following:

EXAMPLE

PDT treatment of acute methicillin resistant *Staphylococcus aureus* wound infection models using methylene blue as a photosensitizing agent advantageously provided destruction of the infection cells. Results of testing include determination of the optimal light dose and specific dye concentration to achieve eradication of *Staphylococcus aureus* in an acute wound infection model; determination of acute gross morphologic and histologic effects of PDT treatment on tissues; and determination of optimum light delivery to acutely and chronically infected tissues.

The wound models were divided into 13 groups. Two of the thirteen groups were not treated with any dye. The other eleven groups were treated with various concentrations of toluidene or methylene blue. The wound models were then exposed to various amounts of activating laser light to determine the optimal dye and light dose for antisepsis.

Thirty nine wound models were innoculated with methicillin resistant *Staphylococcus aureus* quantified at $10^9$ CFU/ml matched to a McFarland standard. The wounds were dressed open with a sterile bioclusive dressing. Testing was performed on uniform wound defects having about a 2×2 cm window of tissue. The volume of solutions placed into the wounds was about 0.1 ml of bacterial innoculum and 0.1 ml of dye.

Four hours later, the wounds were treated with different concentrations of either methylene blue or toluidene blue; 50, 100, 150, 200, 250, 340 or 400 µg/ml and different total light doses; 0, 30 or 60 Joules/cm$^2$. Methylene blue was activated at 664 nm light and toluidine blue was activated at 630 nm light using an argon pumped dye laser. The light delivery was via a microlens fiber tip for surface applications to treat a 4 cm spot. Immediately after treatment, all wounds were sutured closed.

Ninety six hours after inoculation, all wounds were sterilely reopened and cultured. Histology of all wound models was performed using hematoxylin and eosin staining using standard techniques and evaluated by a clinical pathologist. A comparison of bacterial counts related to different dye and light treatment combinations were made. Also a comparison of gross morphologic and microscopic changes between each treatment group was performed. Statistical analysis was performed by a biostatistician.

Statistical comparisons were made of bacterial growth (log cfu), dye concentration (µg/ml), total light dose (Joules/cm$^2$), and dose rate (mw/cm$^2$) groups. Bacterial counts were averaged for each group.

Results of in-vivo testing of methylene blue* is shown below in Table 1.

TABLE 1

| Group | Concentration µg/ml | Total Light Dose | Dose Rate | Bacterial Count log CFU Mean (SD) | Significant Difference** |
|---|---|---|---|---|---|
| 1 | 50 | 30 | 100 | 5.62 (.709) | 6,7,8 |
| 2 | 100 | 30 | 100 | 5.55 (.566) | 6,7,8 |
| 3 | 150 | 60 | 100 | 4.35 (.531) | 6,9,10 |
| 4 | 200 | 60 | 100 | 4.29 (.192) | 6,9,10 |
| 5 | 150 | 60 | 150 | 4.78 (.805) | 6,8 |
| 6 | 250 | 60 | 150 | 2.57 (.552) | 1,2,3,4,5,9,10 |
| 7 | 340 | 60 | 150 | 3.51 (.154) | 1,2,9,10 |
| 8 | 400 | 60 | 150 | 2.99 (.368) | 1,2,5,9,10 |
| 9 | 250 | 0 | 0 | 5.93 (.242) | 3,4,6,7,8 |
| 10 | 0 | 0 | 0 | 6.06 (.102) | 3,4,6,7,8 |

*The one-way ANOVA for the difference between the mean bacterial growth for the ten groups was significant with a p-value = 0.001.
**The group numbers indicated are those that are significantly different for this group (p < 0.05) using Tukey's method of adjusting for multiple comparisons in order to maintain an overall alpha of 0.05.

*Statistically significant observations for photodynamic therapy methylene blue treatment of *staphylococcus aureus* tissue infection are as follows:

Groups 9 and 10 (dye concentration and/or light dose=0) had significantly more bacteria than all groups with a concentration of methylene blue greater than 150 µg/ml.

Groups 6, 7 and 8, with the highest concentration of methylene blue (>200 µg/ml) had fewer bacteria than groups with concentrations under 150 µg/ml or a light dose of 0.

Group 6 had the lowest bacterial growth, with a concentration of methylene blue of 250 µg/ml. This group was significantly different than all groups with the concentration of methylene blue less than µg/ml. Concentrations greater than 250 µg/ml did not appear to offer any benefit in terms of bacterial reduction.

Comparing groups 3 and 5 (concentration 150 µg/ml and total light dose 60 Joules/cm$^2$) demonstrated that the light dose rate of 150 versus 100 mw/cm$^2$ was not significant.

It was difficult to evaluate the effect of increasing the total light dose from 30 to 60 Joules/cm$^2$ since these two doses were not used while holding the dye concentration and dose rate constant.

*In summary, the optimal methylene blue dye concentration, total light dose and dose rate required to maximally and significantly reduce (p<0.05) the bacterial growth (3.49 log CFU reduction) in a methicillin resistant staphylococcus wound infection was methylene blue 250 µg/ml at a total light dose of 60 J/cm² at a dose rate of 150 mw/cm²

Results of in-vivo testing of toluidine blue* is shown below in Table 2.

TABLE 2

| Group | Concentration μg/ml | Total Light Dose | Dose Rate | Bacterial Count (log CFU) Mean (SD) | Significant Difference** |
|---|---|---|---|---|---|
| 1 | 150 | 60 | 100 | 3.18 (1.685) | |
| 2 | 150 | 60 | 150 | 4.82 (.647) | |
| 3 | 150 | 0 | 0 | 4.33 (.954) | |

*The one-way ANOVA for the difference between the mean bacterial growth for the three groups was not significant with a p-value = 0.291.
**None of the groups were significantly different.

The gross morphologic observations demonstrated no evidence of clinical infection in wounds that cultured less than 3 log CFU bacteria. There was no gross evidence of skin or muscle tissue necrosis. The histologic evaluation, using hematoxylin and eosin staining, of all the photodynamically treated and non-photodynamically treated wounds demonstrated no difference. There was no evidence of microscopic wound tissue necrosis to the skin, muscle or fascia related to the action of methylene blue, toluidine blue and light activation.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. A method of treating an infection or sterilization comprising the steps of:
   identifying an in-vivo area of infection or area of sterilization;
   applying a concentration including a combination of polymyxin B and at least one of methylene blue or toluidene blue to the area of infection or area of sterilization; and
   exposing the area of infection or area of sterilization with a light having a light wavelength, light dosage and a light dosage rate.

2. The method of treating an infection or sterilization of claim 1 wherein the light wavelength ranges from about 610 nm to about 680 nm, the light dosage ranges from about 30 J/cm² to about 60 J/cm² and the light dosage rate ranges from about 50 mw/cm² to about 150 mw/cm².

3. The method of treating an infection or sterilization of claim 2 wherein the concentration ranges from about 10 μg/ml to about 500 μg/ml.

4. The method of treating an infection or sterilization of claim 1 wherein the wavelength ranges from about 630 nm to about 664 nm.

5. The method of treating an infection or sterilization of claim 1 wherein the concentration ranges from about 10 μg/ml to about 250 μg/ml; the light wavelength ranges from about 630 nm to about 670 nm; the light dosage ranges from about 20 J/cm² to about 60 J/cm²; and the light dosage rate ranges from about 50 mw/cm² to about 150 mw/cm².

6. The method of treating an infection or sterilization of claim 1 wherein the concentration ranges from about 50 g/ml to about 250 μg/ml; the light dosage ranges from about 30 J/cm² to about 60 J/cm²; and the light dosage rate ranging from about 100 mw/cm² to about 150 mw/cm².

7. The method of treating an infection or sterilization of claim 6 wherein the concentration is about 250 μg/ml; the light dosage is about 60 J/cm²; and the dosage rate is about 150 mw/cm².

8. The method of treating an infection or sterilization of claim 1 wherein the area of infection or area of sterilization includes a microorganism that is gram positive or gram negative including at least one of staphylococcus, *Candida albicans, Escherichia coli,* enterococcus, streptococcus, *Pseudomanus aeruginosa, Hemophilus influenzae,* or *E-coli.*

9. A infection or sterilization treatment kit comprising:
   a volume of a concentration including a combination of polymyxin B and at least one of methylene blue or toluidene blue, the concentration ranging from about 10 μg/ml to about 500 μg/ml; and
   a light emitting treatment device having a thickness, one or more surfaces and one or more light dosage members disposed therein, the one or more light dosage members configured to emit light at an infection at wavelengths ranging from about 450 nm to about 850 nm; a dosage rate ranging from about 0 to about 150 mw/cm²; and a light dose ranging from 0 to about 300 J/cm².

10. A method of treating an infection or sterilization comprising:
    providing one or more cells;
    disposing a concentration including a combination of polymyxin B and at least one of methylene blue or toluidene blue on the one or more cells;
    applying a light having a wavelength ranging from about 450 nm to about 850 nm; a dosage rate ranging from about 0 to about 150 mw/cm²; and a light dose ranging from 0 to about 300 J/cm² to the one or more cells wherein the combination of light and dye is adapted to cause intracellular enzyme deactivation of the one or more cells.

11. The method of treating an infection or sterilization of claim 10 wherein the light dose is adapted to increase permeability of the one or more cells and cause diffusion of the dye into the one or more cells.

12. The method of treating an infection or sterilization of claim 10 wherein the one or more cells are at least one of a bacteria or a fungus.

13. The method of treating an infection or sterilization of claim 10 wherein the one or more cells are gram positive or gram negative.

14. The method of treating an infection or sterilization of claim 10 wherein the dye is monomeric or dimeric.

15. The method of treating an infection or sterilization of claim 10 wherein the dye is adapted to attach at hydrophobic or hydrophilic sites at the one or more cells.

16. The method of treating an infection or sterilization of claim 10 wherein the one or more cells include a pathogenic organism selected from the group consisting of *Candida albicans, Escherichia coli,* enterococcus, streptococcus, *Pseudomanus aeruginosa, Hemophilus influenzae,* and *E-coli.*

17. The method of treating an infection or sterilization of claim 10 wherein as the concentration of dye disposed on the one or more cells is increased a proportional total concentration of light is applied to the one or more cells.

18. The method of treating an infection or sterilization of claim 10 wherein the concentration of dye is fixed and wherein as the concentration of the bacteria or fungus is increased, a proportionally increased total light dose administration is provided for eradication of the bacteria or fungus.

19. The method of treating an infection or sterilization of claim 10 wherein the infection is in-vivo or in-vitro.

* * * * *